United States Patent
Chen et al.

(10) Patent No.: US 8,957,227 B2
(45) Date of Patent: Feb. 17, 2015

(54) PREPARATION OF DULOXETINE® HYDROCHLORIDE USING OPTICALLY ACTIVE METHYLHYDROXYLAMINOPROPANOL COMPOUND AS AN INTERMEDIATE

(71) Applicant: SCI Pharmtech, Inc., Taoyuan County (TW)

(72) Inventors: Bo-Fong Chen, Taoyuan (TW); Feng-Ju Lu, Taoyuan (TW); Jinun-Ban Yeh, Taoyuan (TW); Wei-Chyun Wong, Taoyuan (TW); Feng-hsu Li, Taoyuan (TW); Yen-Wei Li, Taoyuan (TW); Yeh-Chi Su, Taoyuan (TW)

(73) Assignee: SCI Pharmtech, Inc. (TW)

( * ) Notice: Subject to any disclaimer, the term of this patent is extended or adjusted under 35 U.S.C. 154(b) by 0 days.

(21) Appl. No.: 14/014,058

(22) Filed: Aug. 29, 2013

(65) Prior Publication Data

US 2014/0005414 A1    Jan. 2, 2014

Related U.S. Application Data

(63) Continuation-in-part of application No. 12/774,933, filed on May 6, 2010, now Pat. No. 8,530,674.

(51) Int. Cl.
  *C07D 333/22*    (2006.01)
  *C07D 333/20*    (2006.01)
(52) U.S. Cl.
  CPC ................................. *C07D 333/20* (2013.01)
  USPC ........................................................... 549/72
(58) Field of Classification Search
  None
  See application file for complete search history.

*Primary Examiner* — Heidi Reese
(74) *Attorney, Agent, or Firm* — Berliner & Associates

(57) ABSTRACT

The present invention provides a process for preparing duloxetine hydrochloride with higher yield and lower cost.

20 Claims, No Drawings

PREPARATION OF DULOXETINE® HYDROCHLORIDE USING OPTICALLY ACTIVE METHYLHYDROXYLAMINOPROPANOL COMPOUND AS AN INTERMEDIATE

This application is a continuation in part application of U.S. patent application Ser. No. 12/774,933, filed on May 6, 2010 and incorporated herein for reference in its entirety.

BACKGROUND OF THE INVENTION

1. Field of the Invention

The present invention relates to preparation of (S)-(+)-N-methyl-3-(1-naphthyloxy)-3-(2-thienyl)propylamine (Duloxetine®). Particularly, this invention relates to the preparation of duloxetine hydrochloride.

2. Description of Related Art (S)-(+)-N-methyl-3-(1-naphthyloxy)-3-(2-thienyl)propylamine (Duloxetine®) is used as an antidepressant drug in the form of hydrochloride salt. US2007/0167636 discloses a process for the preparation of duloxetine by reacting (S)-(−)-3-methylamino-1-(2-thienyl)propan-1-ol with 1-fluoronaphthalene, in the presence of potassium hydroxide and in a mixture of DMSO and toluene. In this process, the reaction is carried out in a mixed solvent system of toluene and DMSO, preferably with greater ratio by volume. However, carrying out the reaction in this solvent system is time consuming. Moreover, more working procedure is required in order to obtain a product of high quality.

In addition, WO2007/148103 discloses a method for preparing crystalline duloxetine hydrochloride. In this case, the duloxetine is purified by being crystallized from an ethanol solution with 20% hydrochloric acid as the chlorinating agent, such that crystalline duloxetine hydrochloride with about 55% yield is obtained. Furthermore, U.S. Pat. No. 5,362,886 discloses that duloxetine hydrochloride is obtained by adding concentrated hydrochloric acid to a solution of duloxetine base in ethyl acetate. However, the preparation of duloxetine hydrochloride by using hydrochloride acid as the chlorinating agent results in low yield of duloxetine hydrochloride due to high solubility of duloxetine hydrochloride in water.

WO2007/148102 further provides a method for the preparation of crystalline duloxetine hydrochloride, in which gaseous hydrochloride is introduced into an organic solution of duloxetine. However, the gaseous hydrochloride is dangerous to handle.

SUMMARY OF THE INVENTION

In light of the above-mentioned drawbacks of the prior arts, the present invention provides a simple and safe process for the preparation of (S)-(+)-N-methyl-3-(1-naphthyloxy)-3-(2-thienyl)propylamine (Duloxetine®) hydrochloride with high purity and yield.

In accordance with the present invention, a process for preparing (S)-(+)-N-methyl-3-(1-naphthyloxy)-3-(2-thienyl) propylamine hydrochloride includes steps of: (a) dissolving (S)-(+)-N-methyl-3-(1-naphthyloxy)-3-(2-thienyl)propylamine in an organic solvent to form a mixture, wherein the organic solvent is at least one of $C_{3-8}$ ketones; and (b) adding anhydrous hydrochloric acid to the mixture, wherein the anhydrous hydrochloric acid is formed by reacting acyl chloride with alcohol.

In accordance with the present invention, the (S)-(+)-N-methyl-3-(1-naphthyloxy-3-(2-thienyl)propylamine is dissolved in acetone to form a mixture.

In an embodiment of the present invention, the acyl chloride is represented by the formula of $R_1COCl$, and wherein $R_1$ is selected from H, $C_{1-6}$ alkyl group; thionyl chloride ($SOCl_2$) and phosphoryl chloride ($POCl_3$).

In an embodiment of the present invention, the alcohol is represented by the formula of $R_2OH$, and wherein $R_2$ is $C_{1-8}$ alkyl group.

In accordance with the present invention, the (S)-(+)-N-methyl-3-(1-naphthyloxy)-3-(2-thienyl)propylamine is prepared by a process comprising steps of:

(i) performing a Mannich reaction of 2-acetylthiophene, formaldehyde and a compound represented by the formula of $HNCH_3(OR)$, to form a compound of formula (I);

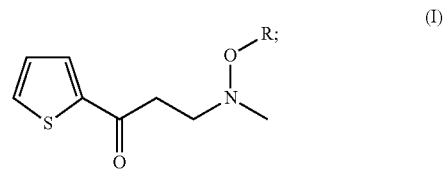

(ii) enantioselectively reducing the compound of formula (I) to a compound of formula (II);

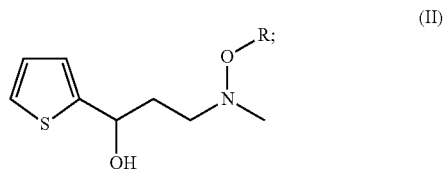

(iii) performing an N,O-cleavage reaction on the compound of formula (II) to form (S)-(−)-3-methylamino-1-(2-thienyl)propan-1-ol of formula (III);

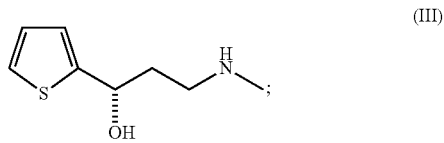

and (iv) reacting the (S)-(−)-3-methylamino-1-(2-thienyl)propan-1-ol of formula (III) with halonaphthalene to form (S)-(+)-N-methyl-3-(1-naphthyloxy)-3-(2-thienyl)propylamine of the following formula;

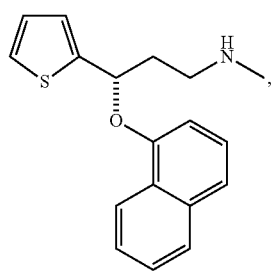

wherein R is a hydrogen atom, $C_{1-8}$ alkyl or $C_{6-10}$ aryl and halo is F, Cl, Br or I.

This invention provides an improved process for preparing duloxetine hydrochloride. In accordance with the present invention, an anhydrous hydrochloric acid is formed by reacting acyl chloride with alcohol in acetone. The present invention provides advantages of providing a pure crystalline form of duloxetine hydrochloride by using an acyl chloride as the chlorinating agent in place of concentrated hydrochloric acid or gaseous hydrochloric acid to the process of the present invention provides good yield of duloxetine hydrochloride, and is more convenient to perform on a large scale.

DETAILED DESCRIPTION OF PREFERRED EMBODIMENTS

The following embodiments are provided to illustrate the disclosure of the present invention, these and other advantages and effects can be understood by those skilled in the art after reading the disclosure of this specification. The present invention can also be achieved by or applied to other embodiments. The details of this specification may be based on different points and applications, and numerous modifications and variations can be devised without departing from the spirit of the present invention.

The present invention provides a process for preparing (S)-(+)-N-methyl-3-(1-naphthyloxy)-3-(2-thienyl)propylamine hydrochloride, which comprises steps of: (a) dissolving (S)-(+)-N-methyl-3-(1-naphthyloxy)-3-(2-thienyl)propylamine in an organic solvent to form a mixture, wherein the organic solvent is at least one of $C_{3-8}$ ketones; and (b) adding anhydrous hydrochloric acid to the mixture, wherein the anhydrous hydrochloric acid is formed by reacting acyl chloride with alcohol.

In one embodiment of the present invention, in the step (a), the (S)-(+)-N-methyl-3-(1-naphthyloxy)-3-(2-thienyl)propylamine is dissolved in an organic solvent selected from $C_{3-8}$ ketones and combination thereof, to form a mixture. In another embodiment of the present invention, in the step (a), the (S)-(+)-N-methyl-3-(1-naphthyloxy)-3-(2-thienyl)propylamine is dissolved in an organic solvent comprising at least acetone to form a mixture. In yet another embodiment of the present invention, in the step (a), the (S)-(+)-N-methyl-3-(1-naphthyloxy)-3-(2-thienyl)propylamine is dissolved in acetone to form a mixture.

According to the step (a) of the present invention, the (S)-(+)-N-methyl-3-(1-naphthyloxy)-3-(2-thienyl)propylamine is dissolved in an organic solvent by heating. In one embodiment of the present invention, the (S)-(+)-N-methyl-3-(1-naphthyloxy)-3-(2-thienyl)propylamine is dissolved in an organic solvent to form a mixture by heating, at about 50° C.

According to the step (b) of the present invention, anhydrous hydrochloride is added to the mixture of the step (a).

The anhydrous hydrochloric acid used in the step (b) is formed by reacting acyl chloride with alcohol.

In one embodiment of the present invention, the acid chloride is represented by the formula of $R_1COCl$ wherein $R_1$ is selected from H, $C_{1-6}$ alkyl group, thionyl chloride ($SOCl_2$) and phosphoryl chloride ($POCl_3$).

In one embodiment of the present invention, the alcohol is represented by the formula of $R_2OH$, wherein $R_2$ is $C_{1-8}$ alkyl, and preferably, $R_2$ is $C_{1-6}$alkyl.

In one embodiment of the present invention, anhydrous hydrochloride is added to the mixture of the step (a) until the pH reaches about 5.5 to 7.5.

In one embodiment of the present invention, anhydrous hydrochloric acid is added to the mixture of the step (a) by heating. In another embodiment of the present invention, anhydrous hydrochloric acid is added to the mixture of the step (a) and then heated to the temperature at a range from about 40° C. to 60° C., preferably at about 50° C.

It has been a long standing need to provide a process for the preparation of duloxetine hydrochloride so as to overcome the problems presented in conventional processes, such as the usage of gaseous hydrochloric acid which is expensive and dangerous and the usage of concentrated hydrochloric acid which leads to poor yield of duloxetine hydrochloride. The preparation process according to the present invention can at least overcome the aforementioned problems by, for example, reacting free duloxetine with anhydrous hydrochloride formed by acid chloride and alcohol in the presence of acetone.

In one embodiment of the present invention, the (S)-(+)-N-methyl-3-(1-naphthyloxy)-3-(2-thienyl)propylamine used in the present invention may be prepared by a process, in which a compound represented by formula (II) is described hereafter and is used as an intermediate.

In one embodiment of the present invention, for preparation of (S)-(+)-N-methyl-3-(1-naphthyloxy)-3-(2-thienyl)propylamine (Duloxetine®), a compound of formula (II) is provided in an optically active form:

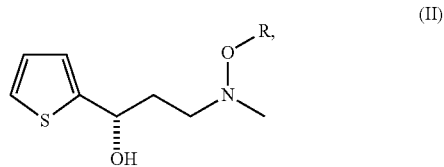

(II)

wherein R is a hydrogen atom, $C_{1-8}$ alkyl or $C_{6-10}$ aryl. Furthermore, the absolute configuration of the chiral center is S.

R in the above formula (II) is preferably an alkyl group having 1 to 4 carbon atoms, and more preferably, R is a methyl group.

In one embodiment of the present invention, (S)-(+)-N-methyl-3-(1-naphthyloxy)-3-(2-thienyl)propylamine (Duloxetine®) is prepared by using (S)-(−)-3-methylamino-1-(2-thienyl)propan-1-ol of formula (III) described hereafter, which is produced from the compound of formula (II), thereby higher yield can be obtained at a lower cost.

According to one embodiment of the present invention, the (S)-(+)-N-methyl-3-(1-naphthyloxy)-3-(2-thienyl)propylamine can be prepared by a process comprising steps of:

(i) performing a Mannich reaction of 2-acetylthiophene, formaldehyde and a compound of formula $HNCH_3(OR)$ to form a compound of formula (I);

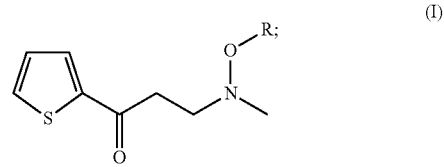

(I)

(ii) enantioselectively reducing the compound of formula (I) to a compound of formula (II):

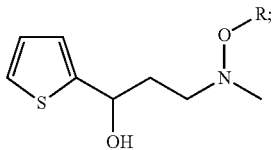

(iii) performing an N,O-cleavage reaction on the compound of formula (II) to form (S)-(−)-3-methylamino-1-(2-thienyl)propan-1-ol of formula (III);

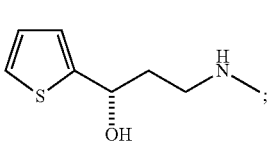

and (iv) reacting the (S)-(−)-3-methylamino-1-(2-thienyl)propan-1-ol of formula (III) with halonaphthalene to form (S)-(+)-N-methyl-3-(1-naphthyloxy)-3-(2-thienyl)propylamine of the following formula:

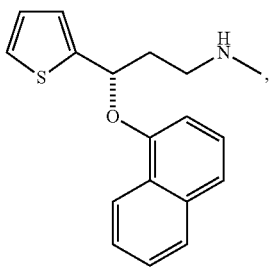

wherein R is a hydrogen atom, $C_{1-8}$ alkyl or $C_{6-10}$ aryl; and halo is F, Cl, Br or I.

In one embodiment of the present invention, the compound of formula (I) obtained in the step (i) is as a free form or as an acid addition salt.

In one embodiment of the present invention, the step (i) is performed at a temperature ranging from 15° C. to 90° C., preferably from 40° C. to 80° C., and more preferably from 50° C. to 70°. The reduction of the compound of formula (I) in the step (ii) is performed by asymmetric reduction, and the resulting optically active form of the compound of formula (II) is obtained. The optically active form can be obtained via asymmetric hydrogenation using catalyst with chiral ligands or hydride with chiral ligands.

In one embodiment of the present invention, the step (ii) is performed by chiral reduction. In one embodiment of the present invention, the step (ii) is performed in the presence of $RuCl_2((R)$-3,5-xylylBINAP)DIAPEN. In one embodiment of the present invention, the step (ii) is performed in the presence of a reduction catalyst comprising an enantiomer-enriched bidentate phosphorus-containing ligand, a transition metal and a diamine, preferably a chiral diamine.

In one preferred embodiment, reduction of the compound of formula (I) in the step (ii) is carried out in a mixture of an alcohol such as methanol and a base such as potassium tert-butoxide, in the presence of a catalyst that comprises an enantiomer-enriched bidentate phosphorus-containing ligand, a transition metal and a diamine, preferably a chiral diamine, such as $RuCl_2((R)$-3,5-xylylBINAP) ((2R)-DAIPEN). The reaction mixture is hydrogenated at predetermined pressure to yield (S)-methylhydroxylaminopropanol with high ee value.

The step (ii) can be performed at a pH ranging from pH 6 to 14.

According to the present invention, the N,O-cleavage reaction of the compound of formula (II) in the step (iii) is carried out by hydrogenation. The N,O-cleavage reaction in the step (iii) is carried out by hydrogenation in the presence of a catalyst such as Raney-nickel, or by chemical reduction methods such as those using $LiAlH_4$ or zinc metal as the reducing agent.

In one embodiment of the present invention, the N,O-cleavage reaction of the compound of formula (II) in the step (iii) is carried out by hydrogenation in an alcohol, in the presence of Raney-nickel catalyst, at a temperature ranging from 15□ to 80□.

In one embodiment of the present invention, the N,O-cleavage reaction of the compound of formula (II) in the step (iii) is carried out by a chemical reduction using $LiAlH_4$ or zinc metal as the reducing agent.

According to the present invention, in the step (iv), (S)-(−)-3-methylamino-1-(2-thienyl)propan-1-ol of formula (III) is reacted with halonaphthalene, preferably 1-fuloronaphthalene.

In one embodiment of the present invention, the (S)-(−)-3-methylamino-1-(2-thienyl)propan-1-ol of formula (III) is reacted with excess 1-fuloronaphthalene in a solvent such as DMSO.

In one embodiment of the present invention, DMSO is used in an amount ranging from one to ten times the amount of (S)-(−)-3-methylamino-1-(2-thienyl)propan-1-ol of formula (III).

In one embodiment of the present invention, DMSO is used in an amount ranging from one to five times the amount of (S)-(−)-3-methylamino-1-(2-thienyl)propan-1-ol of formula (III).

According to the present invention, in step (iv), (S)-(−)-3-methylamino-1-(2-thienyl)propan-1-ol of formula (III) can be reacted with halonaphthalene in the presence of a base. In one embodiment of the present invention, a base of formula $KOR_3$ can be used, wherein $R_3$ is C1-6 alkyl. In one embodiment of the present invention, potassium tert-butoxide is used as a base in the step (iv).

The excess amount of halonaphthalene, such as from ranging from about 1.5 to 4 equivalents, can be recovered for future use. The reaction is performed at a temperature ranging from 20° C. to 110° C., preferably from 40° C. to 90° C., for 1 to 24 hours. In one embodiment of the present invention, the reaction is conducted in the presence of excess halonaphthalene and a suitable amount of DMSO in order to overcome the problems regarding racemization and environmental protection associated with conventional preparation methods.

The present invention further provides a process for preparing (S)-(+)-N-methyl-3-(1-naphthyloxy)-3-(2-thienyl)propylamine hydrochloride, comprising steps of:

(i) performing a Mannich reaction of 2-acetylthiophene, formaldehyde and a methylhydroxylamine of formula $HNCH_3(OR)$, to form a compound of formula (I);

(ii) enantioselectively reducing the compound of formula (I) to a compound of formula (II);

(iii) performing an N,O-cleavage reaction of the compound of formula (II) to form (S)-(−)-3-methylamino-1-(2-thienyl)propan-1-ol of formula (III); and (iv) reacting the (S)-(−)-3-methylamino-1-(2-thienyl)propan-1-ol of formula (III) with halonaphthalene to form (S)-(+)-N-methyl-3-(1-naphthyloxy)-3-(2-thienyl)propylamine; and (v) dissolving (S)-(+)-N-methyl-3-(1-naphthyloxy)-3-(2-thienyl)propylamine in an organic solvent to form a mixture, wherein the organic solvent is at least one of $C_{3-8}$ ketones; and (vi) adding anhydrous hydrochloric acid to the mixture, wherein the anhydrous hydrochloric acid is formed by reacting acyl chloride with alcohol;

wherein R is a hydrogen atom, $C_{1-8}$ alkyl or $C_{6-10}$ aryl; and halo is F, Cl, Br or I.

According to one embodiment of the present invention, the step (i) of the process is carried out at a temperature ranging from 15° C. to 90° C., preferably from 40° C. to 80° C., and more preferably from 50° C. to 70° C. The compound of the formula (I) obtained in the step (i) is either as a free form or as an acid addition salt.

The reduction of the compound of formula (I) in the step (ii) is performed by asymmetric reduction, and the resulting optically active form of the compound of formula (II) is obtained. The optically active form can be obtained via asymmetric hydrogenation using catalyst with chiral ligands or hydride with chiral ligands.

In one embodiment of the present invention, the step (ii) is performed by chiral reduction. In one embodiment of the present invention, the step (ii) is performed in the presence of $RuCl_2((R)$-3,5-xylylBINAP)DIAPEN. In one embodiment of the present invention, the step (ii) is performed in the presence of a reduction catalyst comprising an enantiomer-enriched bidentate phosphorus-containing ligand, a transition metal and a diamine, preferably a chiral diamine.

In one preferred embodiment, the reduction of the compound of formula (I) in the step (ii) is carried out in a mixture of an alcohol such as methanol and a base such as potassium tert-butoxide, in the presence of a catalyst that comprises an enantiomer-enriched bidentate phosphorus-containing ligand, a transition metal and a diamine; preferably a chiral diamine, such as $RuCl_2((R)$-3,5-xylylBINAP) ((2R)-DAIPEN). The reaction mixture is hydrogenated at predetermined pressure to yield (S)-methylhydroxylaminopropanol with high ee value.

The step (ii) can be performed at a pH value ranging from 6 to 14.

According to the present invention, the N,O-cleavage reaction of the compound of formula (II) in the step (iii) is carried out by hydrogenation. The N,O-cleavage reaction in the step (iii) is carried out by hydrogenation in the presence of a catalyst such as Raney-nickel, or by chemical reduction methods such as those using $LiAlH_4$ or zinc metal as the reducing agent.

In one embodiment of the present invention, the N,O-cleavage reaction of the compound of formula (II) in the step (iii) is carried out by hydrogenation in an alcohol, in the presence of Raney-nickel catalyst at a temperature ranging from 15° C. to 80° C.

In one embodiment of the present invention, the N,O-cleavage reaction of the compound of formula (II) in the step (iii) is carried out by a chemical reduction using $LiAlH_4$ or zinc metal as the reducing agent.

According to the present invention, in step (iv), (S)-(−)-3-methylamino-1-(2-thienyl)propan-1-ol of formula (III) is reacted with halonaphthalene, preferably 1-fuloronaphthalene.

In one embodiment of the present invention, the (S)-(−)-3-methylamino-1-(2-thienyl)propan-1-ol of formula (III) is reacted with excess 1-fuloronaphthalene in a solvent such as DMSO.

In one embodiment of the present invention, DMSO is used in an amount ranging from one to ten times the amount of (S)-(−)-3-methylamino-1-(2-thienyl)propan-1-ol of formula (III).

In one embodiment, of the present invention, DMSO is used in an amount ranging from one to five times the amount of (S)-(−)-3-methylamino-1-(2-thienyl)propan-1-ol of formula (III).

According to the present invention, in step (iv), (S)-(−)-3-methylamino-1-(2-thienyl)propan-1-ol of formula (III) can be reacted with halonaphthalene in the presence of a base. In one embodiment of the present invention, a base of formula $KOR_3$ can be used, wherein $R_3$ is C1-6 alkyl. In one embodiment of the present invention, potassium tert-butoxide is used as a base in step (iv).

In one preferred embodiment, in step (iv), the reaction of (S)-(−)-3-methylamino-1-(2-thienyl)propan-1-ol of formula (III) with an excess of halonaphthalene to give (S)-(+)-N-methyl-3-(1-naphthyloxy)-3-(2-thienyl)propylamine (duloxetine) is carried out by using potassium tert-butoxide in a suitable amount of DMSO. The excess amount of halonaphthalene, such as from 1.5 to 4 equivalents, can be recovered for use again. The reaction is performed at a temperature ranging from 20° C. to 110° C. preferably from 40° C. to 90° C., for 1 to 24 hours. In one embodiment of the present invention, the reaction is conducted in the presence of excess halonaphthalene and a suitable amount DMSO, in order to overcome the problems regarding racemization and environmental protection associated with conventional preparation methods.

The preparation and purification of duloxetine hydrochloride comprises the step (v) dissolving (S)-(+)-N-methyl-3-(1-naphthyloxy)-3-(2-thienyl)propylamine in an organic solvent to form a mixture, wherein the organic solvent is at least one of $C_{3-8}$ ketones; and the step (vi) adding anhydrous hydrochloric acid to the mixture, wherein the anhydrous hydrochloric acid is formed by reacting acyl chloride with alcohol.

According to the present invention, an acyl chloride and an alcohol is applied to form fresh anhydrous hydrochloric acid, which adding to duloxetine free base to form hydrochloride.

In one embodiment of the present invention, in the step (v), the (S)-(+)-N-methyl-3-(1-naphthyloxy)-3-(2-thienyl)propylamine is dissolved in an organic solvent selected from C3-8 ketones and combination thereof, to form a mixture. In another embodiment of the present invention, in the step (v), the (S)-(+)-N-methyl-3-(1-naphthyloxy)-3-(2-thienyl)propylamine is dissolved in an organic solvent comprising at least acetone to form a mixture. In yet another embodiment of the present invention, in the step (v), the (S)-(+)-N-methyl-3-(1-naphthyloxy)-3-(2-thienyl)propylamine is dissolved in acetone to form a mixture.

According to the present invention, in the step (v), the (S)-(+)-N-methyl-3-(1-naphthyloxy)-3-(2-thienyl)propylamine is dissolved in an organic solvent by heating. In one embodiment of the present invention, the (S)-(+)-N-methyl-3-(1-naphthyloxy)-3-(2-thienyl)propylamine is dissolved in an organic solvent to form a mixture by heating, at a temperature of about 50° C.

According to the present invention, in step (vi), an anhydrous hydrochloride is added to the mixture of the step (v). The anhydrous hydrochloride used in the step (vi) is formed by an acid chloride and an alcohol.

In one embodiment of the present invention, the acid chloride is represented by the formula of $R_1COCl$, wherein $R_1$ is selected from H, $C_{1-6}$ alkyl; thionyl chloride ($SOCl_2$) and phosphoryl chloride ($POCl_3$).

In one embodiment of the present invention, the alcohol is represented by the formula of $R_2OH$, wherein $R_2$ is $C_{3-6}$ alkyl.

In one embodiment of the present invention, anhydrous hydrochloride is added to the mixture of the step (v) until the pH reaches about 5.5 to about 7.5.

In one embodiment of the present invention, anhydrous hydrochloride is added to the mixture of the step (v) by heating. In another embodiment of the present invention, anhydrous hydrochloride is added to the mixture of the step (v) and then heated the temperature at 40° C. to 60° C., preferably at about 50° C.

According to one embodiment of the present invention, the above process is summarized in Scheme 1. In Scheme 1, R is a hydrogen atom, $C_{1-8}$ alkyl or $C_{6-10}$ aryl; and X is halo. Preferably X is F, Cl, Br or I.

ates particularly well on an industrial scale, in view of economic and environmental friendly aspects.

EXAMPLES

Example 1

Synthesis of 3-methoxymethylamino-1-(2-thienyl)-1-propanone hydrochloride salt

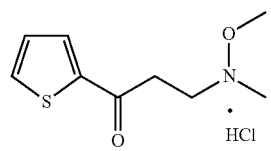

27.7 g of N,O-dimethylhydroxylamine hydrochloride, 9.3 g of paraformaldehyde, 6.4 g of 32% hydrochloric acid, 30.0 g of 2-acetylthiophene and 100 g of isopropanol were pro- Scheme 1

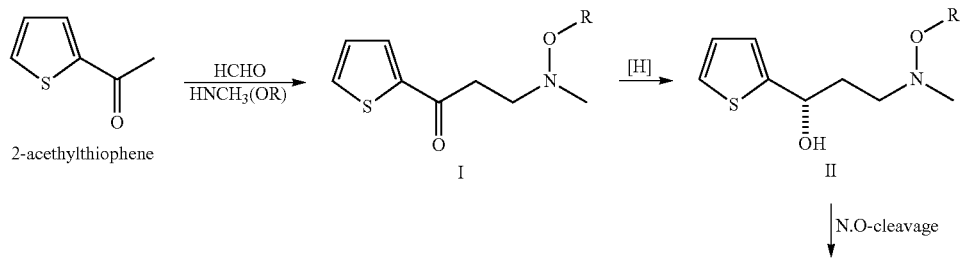

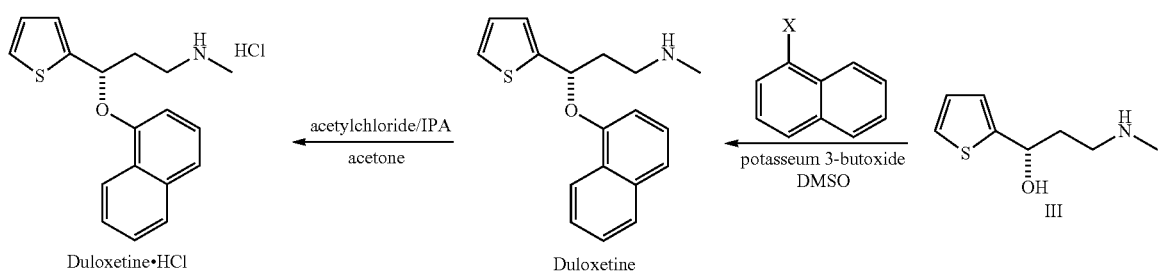

The above process for preparing duloxetine hydrochloride involves the application of fresh anhydrous hydrochloric acid. Anhydrous hydrochloric acid is generated in situ by reacting acyl chloride with alcohol. The fresh anhydrous hydrochloric acid generated in situ is then reacted with free duloxetine in the presence of a suitable anti-solvent such as acetone to form duloxetine hydrochloride.

In comparison with conventional processes, duloxetine hydrochloride can be obtained in an optically pure form, with higher yield and at a lower cost according to the process of the present invention. The process of the present invention opervided into a flask. After being stirred at 60° C. for 13 hours, the reaction mixture was cooled down to room temperature. The crystal thus formed was filtered, washed with 30 g of isopropanol and dried under reduced pressure to obtain 42.5 g of 3-methoxymethylamino-1-(2-thienyl)-1-propanone hydrochloride salt (75.9%).

$^1$H NMR (400 MHz, $CDCl_3$) δ (ppm)=3.1 (s, 3H), 3.7-3.8 (br, 4H), 4.1 (s, 3H), 7.2 (t, J=4.5 Hz, 1H), 7.7 (d, J=4.9 Hz, 1H), 7.9 (d, J=3.5 Hz, 1H).

Example 2

Synthesis of (S)-3-methoxymethylamino-1-(2-thienyl)propan-1-ol

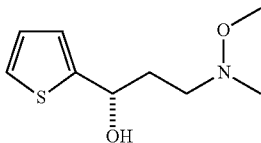

A degassed methanol solution (4 mL) containing RuCl₂ ((R)-3,5-xylylBINAP) ((2R)-DAIPEN) (10 mg), 3-methoxymethylamino-1-(2-thienyl)-1-propanone (160 mg), potassium tert-butoxide (100 mg) and methanol (10 mL) were charged in a glass autoclave under an argon gas flow. After deaeration and replacement by argon, hydrogen was introduced to a predetermined pressure. The resulting solution was hydrogenated at 20□ for 12 hours. Upon completion of hydrogenation, the reaction mixture was concentrated to give the objective compound as an oily product (161 mg, 95% ee; purity: 95.8% by HPLC assay).

¹H NMR (400 MHz, CDCl₃) δ (ppm)=3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Example 3

Synthesis of (S)-(−)-3-methylamino-1-(2-thienyl)propan-1-ol

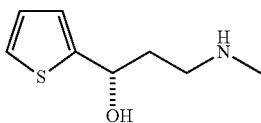

(S)-3-methoxymethylamino-1-(2-thienyl)propan-1-ol obtained in example 2 was dissolved in 10 ml of methanol with 8 mg of Raney-nickel. The resulting solution was provided in a glass autoclave and hydrogenated at 50° C. for 12 hours. Upon completion of hydrogenation, the reaction mixture was filtered and the solvent was removed under reduced pressure to obtain the objective compound as a crystal compound (122 mg, 95% ee; purity; 90.8% by HPLC assay). The crude product was further purified by re-crystallization in toluene to give a product with optical purity as high as 100% ee.

Example 4

Synthesis of (S)-(+)-N-methyl-3-methyl-3-(1-naphthyloxy)-3-(1-naphthyloxy)-3-(2-thienyl)propylamine (Duloxetine®)

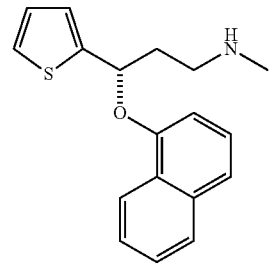

(S)-(−)-3-methylamino-1-(2-thienyl)propan-1-ol (20.0 g) and 1-fuloronaphthalene (68.3 g) were charged in a 4-neck round flask. Potassium tert-butoxide (13.1 g) and DMSO (36.0 g) were added to the reaction, and then heated to a temperature of 60° C. for 8 hours. After completion of the reaction, the mixture was cooled down, and extracted with ethyl acetate. The organic layer was then extracted with water followed by HCl₍aq₎ (14.7 g) to separate duloxetine from excess 1-fluoronaphthalene that remained in the reaction. Duloxetine in acidic aqueous layer was then extracted back to ethyl acetate by adjusting pH value to about 12 with NaOH₍aq₎ (17.6 g). The organic solution was finally concentrated under reduced pressure to give high optical purity objective compound as an oily crude duloxetine.

¹H NMR (400 MHz, CDCl₃) δ (ppm)=2.2 (m, 1H), 2.4 (m, 1H), 2.4 (s, 3H), 2.8 (m, 2H), 5.8 (m, 1H), 6.8 (d, 1H), 6.9 (m, 1H), 7.1 (d, 1H), 7.2 (d, 1H), 7.3 (d, 1H), 7.4 (m, 1H), 7.5 (m, 2H), 7.8 (m, 1H), 8.3 (m, 1H).

Example 5

Synthesis of (S)-(+)-N-methyl-3-methyl-3-(1-naphthyloxy)-3-(2-thienyl)propylamine hydrochloride (Duloxetine.HCl)

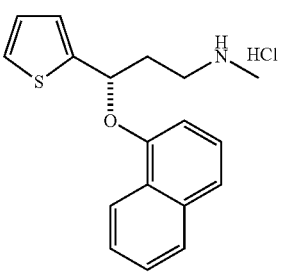

The crude wet duloxetine free base (205.0 g) and an acetone (anti-solvent)(600.0 g) were charged in a 4-neck round flask and heated to a temperature of 50° C. while stirring. To another 4-neck round flask, isopropyl alcohol (IPA) (200.0 g) was charged, and the temperature was set to about 0 to about 5° C. while stirring. Fresh hydrochloride was prepared by dropping acetyl chloride (48.0 g) slowly to the isopropyl alcohol solution and stirring the reaction for one hour at a temperature of about 15° C. to 20° C. Then, the fresh hydrochloric acid in isopropyl alcohol was added to the duloxetine free base solution slowly, and the pH value was controlled in a range from 5.5 to 7.5 with NaOH$_{(aq)}$. The temperature was set at 50° C., and the reaction was gradually cooled to 0° C.~5° C. The reaction was stirred for another one hour at about 0° C.~5° C., and after filtration, the purified duloxetine hydrochloride was produced. (190 g, 99% ee; purity; 98% by HPLC assay).

$^1$H NMR (400 MHz, CDCl$_3$) δ (ppm)=2.2 (m, 1H), 2.4 (m, 1H), 2.4 (s, 3H), 2.8 (m, 2H), 5.8 (m, 1H), 6.8 (d, 1H), 6.9 (m, 1H), 7.1 (d, 1H), 7.2 (d, 1H), 7.3 (d, 1H), 7.4 (m, 1H), 7.5 (m, 2H), 7.8 (m, 1H), 8.3 (m, 1H).

Example 6

Purification of (S)-(+)-N-methyl-3-methyl-3-(1-naphthyloxy)-3-(2-thienyl)propylamine hydrochloride (Duloxetine.HCl)

The duloxetine hydrochloride wet cake (195.0 g), which had 15-20% residue solvent, was dissolved in methanol (250.0 g) at 30° C. and was charcoalized and filtered through celite into another flask. The filtrate was concentrated to strip off about 70 to 80% of MeOH/IPA. Acetone (600.0 g) was added into the duloxetine hydrochloride solution at 42-50° C. The solution was crystallized until the temperature was down to 0-5° C., filtrated, and washed with acetone (150.0 g). The resulting product was dried at 50° C. to get 138 g of purified doluxetine hydrochloride (73% of yield, 99.5% ee, purity: 99% by HPLC assay).

The foregoing descriptions of the detailed embodiments are only illustrated to disclose the features and functions of the present invention, and these descriptions and embodiments are not restrictive to the scope of the present invention. It should be understood by those skilled in the art that all modifications and variations according to the spirit and principles as disclosed in the present invention should fall within the scope of the appended claims.

What is claimed is:

1. A process for preparing (S)-(+)-N-methyl-3-(1-naphthyloxy)-3-(2-thienyl) propylamine hydrochloride, comprising steps of:
   dissolving (S)-(+)-N-methyl-3-(1-naphthyloxy)-3-(2-thienyl) propylamine in an organic solvent to form a mixture, wherein the organic solvent is at least one of C3-8 ketones; and
   adding anhydrous hydrochloric acid to the mixture, wherein the anhydrous hydrochloric acid is formed by an acid chloride and an alcohol.

2. The process according to claim 1, wherein the organic solvent is acetone.

3. The process according to claim 1, wherein the acid chloride is selected from the group consisting of thionyl chloride (SOCl$_2$), phosphoryl chloride (POCl$_3$) and a compound represented by a formula of R$_1$COCl, and wherein R$_1$ is selected from H and C$_{1-6}$ alkyl group.

4. The process according to claim 1, wherein the alcohol is represented by a formula of R$_2$OH, in which R$_2$ is C$_{1-8}$ alkyl.

5. The process according to claim 1, wherein the mixture is heated at 50° C.

6. The process according to claim 1, wherein the anhydrous hydrochloric acid is added to the mixture until a pH value is in a range from 5.5 to 7.5.

7. The process according to claim 1, wherein the anhydrous hydrochloric acid is added to the mixture and then heated at a temperature from 40 to 60° C.

8. The process according to claim 7, wherein the anhydrous hydrochloric acid is added to the mixture and then heated at 50° C.

9. The process according to claim 1, wherein the (S)-(+)-N-methyl-3-(1-naphthyloxy)-3-(2-thienyl) propylamine is prepared by a process comprising steps of:
   performing an N,O-cleavage reaction on the compound of formula (II),

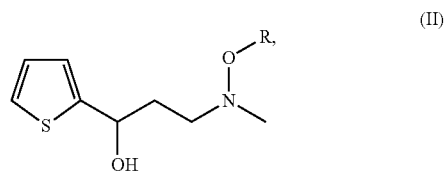

to form (S)-(−)-3-methylamino-1-(2-thienyl)propan-1-ol of formula (III),

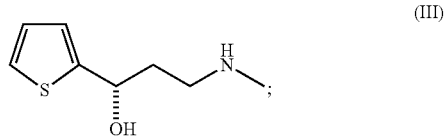

reacting the (S)-(−)-3-methylamino-1-(2-thienyl)propan-1-ol of formula (III) with halonaphthalene and KOR$_3$ in DMSO to form (S)-(+)-N-methyl-3-(1-naphthyloxy)-3-(2-thienyl)propylamine represented by the following formula:

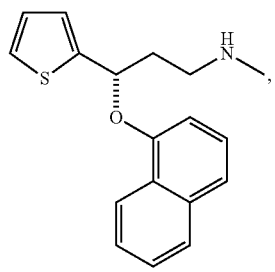

wherein R is a hydrogen atom, C$_{1-8}$ alkyl or C$_{6-10}$ aryl; halo is F, Cl, Br or I; and R$_3$ is C$_{1-6}$ alkyl.

10. The process of claim 9, wherein R is C$_{1-4}$ alkyl.

11. The process of claim 10, wherein R is methyl.

12. The process of claim 9, wherein the halonaphthalene is 1-fluoronaphthalene.

13. The process of claim 9, wherein R$_3$ is tert-butyl.

14. The process of claim 9, wherein the reaction of the (S)-(−)-3-methylamino-1-(2-thienyl)propan-1-ol with halonaphthalene is carried out in presence of excess halonaphthalene, and wherein DMSO is used in an amount ranging from one to ten times the amount of (S)-(−)-3-methylamino-1-42-thienyl)propan-1-ol.

15. The process of claim 14, wherein DMSO is used in an amount ranging from one to five times the amount of (S)-(−)-3-methylamino-1-(2-thienyl)propan-1-ol.

16. A process for preparing (S)-(+)-N-methyl-3-(1-naphthyloxy)-3-(2-thienyl)propylamine hydrochloride represented by the following formula, comprising steps of:

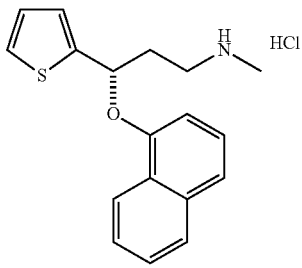

reacting (S)-(−)-3-methylamino-1-(2-thienyl)propan-1-ol with KOR₃ and halonaphthalene in DMSO to form (S)-(+)-N-methyl-3-(1-naphthyloxy)-3-(2-thienyl)propylamine, wherein R₃ is C$_{1-6}$ alkyl; and halo is F, Cl, Br or I;

dissolving the (S)-(+)-N-methyl-3-(1-naphthyloxy)-3-(2-thienyl)propylamine in an organic solvent to form a mixture, wherein the organic solvent is at least one of C$_{3-8}$ ketones; and adding anhydrous hydrochloric acid to the mixture, wherein the anhydrous hydrochloric acid is formed by reacting acyl chloride with alcohol.

17. The process of claim 16, wherein R₃ is tert-butyl.

18. The process of claim 16, wherein the halonaphthalene is 1-fluoronaphthalene.

19. The process of claim 16, wherein the reaction of the (S)-(−)-3-methylamino-1-(2-thienyl)propan-1-ol (III) with KOR₃ and halonaphthalene in DMSO is carried out in presence of excess halonaphthalene, and wherein DMSO is used in an amount ranging from one to ten times the amount of (S)-(−)-3-methylamino-1-(2-thienyl)propan-1-ol.

20. The process of claim 19, wherein DMSO is used in an amount ranging from one to five times the amount of (S)-(−)-3-methylamino-1-(2-thienyl)propan-1-ol.

* * * * *